United States Patent
Du-Nour et al.

(10) Patent No.: US 7,492,467 B1
(45) Date of Patent: Feb. 17, 2009

(54) METHOD AND APPARATUS FOR MEASURING THICKNESS AND OPTICAL PROPERTIES OF A THIN-FILM ON A SUBSTRATE

(75) Inventors: Ofer Du-Nour, Yokne'am (IL); Vladimir Rubinstein, Yokne'am (IL)

(73) Assignee: Nanometrics Incorporated, Milpitas, CA (US)

( * ) Notice: Subject to any disclaimer, the term of this patent is extended or adjusted under 35 U.S.C. 154(b) by 42 days.

(21) Appl. No.: 11/823,452

(22) Filed: Jun. 26, 2007

Related U.S. Application Data (60) Provisional application No. 60/817,014, filed on Jun. 26, 2006, provisional application No. 60/816,893, filed on Jun. 26, 2006, provisional application No. 60/816,815, filed on Jun. 26, 2006.

(51) Int. Cl.
*G01B 11/02* (2006.01)
(52) U.S. Cl. .................................................. 356/504
(58) Field of Classification Search ................ 356/497, 356/503, 504
See application file for complete search history.

(56) References Cited

U.S. PATENT DOCUMENTS

| | | | | |
|---|---|---|---|---|
| 4,558,012 | A * | 12/1985 | Nygren et al. | 436/501 |
| 6,261,665 | B1 * | 7/2001 | Murata et al. | 428/143 |
| 6,985,237 | B2 * | 1/2006 | Mikkelsen et al. | 356/504 |
| 7,324,210 | B2 * | 1/2008 | De Groot et al. | 356/497 |

* cited by examiner

*Primary Examiner*—Michael A Lyons
(74) *Attorney, Agent, or Firm*—Silison Valley Patent Group LLP (57) ABSTRACT

Various embodiments include a metrology tool comprising an emitter configured to emit an incident light beam at a production substrate including an ARL, a receiver configured to receive a reflected light beam from the production substrate, a spectrometer configured to determine a digital signal representing an intensity of a wavelength within the reflected light beam, and a processor configured to determine a spectrum of the reflected light beam from the digital signal, select a suppression band based on an expected wavelength representative of a portion of the ARL, and determine a property of the ARL based on a portion of the spectrum in the selected suppression band.

24 Claims, 7 Drawing Sheets

METHOD AND APPARATUS FOR MEASURING THICKNESS AND OPTICAL PROPERTIES OF A THIN-FILM ON A SUBSTRATE

CROSS-REFERENCE TO RELATED APPLICATIONS

The present application claims the priority benefit of U.S. Provisional Patent Application Ser. No. 60/816,815 filed on Jun. 26, 2006 entitled "Integrating a Metrology Instrument for Multi-film Testing," U.S. Provisional Patent Application Ser. No. 60/817,014 filed on Jun. 26, 2006 entitled "Thickness and Optical Property of a Multi-film Stack Using Wavelength Illumination Filtering for Film Separation," U.S. Provisional Patent Application Ser. No. 60/816,893 filed on Jun. 26, 2006 entitled "System and Methods for Single Wafer Process Control," and U.S. patent application Ser. No. 11/717,327 filed on Mar. 12, 2007 entitled "Method and Apparatus for Process Control With In-Die Metrology," all of which are incorporated by reference herein.

BACKGROUND OF THE INVENTION

1. Field of the Invention

The present invention relates to semiconductor metrology and more particularly to measuring properties of a transparent film on a substrate.

2. Description of Related Art

In a semiconductor manufacturing process of a substrate, a photo-resist layer is applied to a top surface of the substrate. Selected portions of the photo-resist may be exposed to electromagnetic radiation through a lithographic mask and ultimately removed. Ideally, the walls of the photo-resist material remaining after the exposure are smooth and about vertical. However, during exposure of the photo-resist, the light is reflected from the boundary between the photo-resist layer and the surface of the substrate. The reflected light interferes with the incident light in the photo-resist layer causing interference patterns and standing waves. Near the edge of a mask pattern, the interference patterns and standing waves can cause an uneven vertical wall in the photo-resist material after the exposed photo-resist material has been removed. Moreover, features below the surface of the substrate can add additional standing wave patterns creating additional edge roughness in the walls of the photo-resist.

An anti-reflective layer (ARL) may be deposited on the surface of the substrate (between the substrate and the photo-resist layer) to minimize reflections of the light from the surface of the substrate and suppress reflected light from below the substrate surface. The ARL can improve smoothness of the walls of the photo resist.

The ARL properties include, but are not limited to, thickness, reflectivity, refractive index, and extinction coefficient. These properties can be selected and/or adjusted to minimize the reflectivity of the substrate at the wavelength used for exposing the photo-resist. Measurements of the properties of the ARL may be used to adjust and optimize the ARL for suppressing the effects of reflected light at the wavelength used to expose the photo-resist.

One method of measuring the properties of the ARL is to cut (e.g., score and break) the substrate, thus exposing a cross-section of the ARL. The substrate may then be examined using light or scanning electron microscopy (SEM). Unfortunately, the number of features that can be examined may be limited to features lying along the cut. Further, although microscopy can be used to measure the thickness of an ARL, microcopy cannot measure the refractive index or the extinction coefficient. Unfortunately, the substrate is generally destroyed by cutting.

Another method for measuring properties of the ARL includes using a test substrate. A test substrate is a substrate solely used for testing one or more process tools. A substrate is a base layer, surface, semiconductor material, or non-semiconductor material upon which a feature is deposited, removed, etched, attached, or otherwise prepared or fabricated. Examples of a substrate include ceramic, plastic, glass, silicon, germanium, silicon on insulator (SOI), and gallium arsenide.

In one example, the test substrate is used to measure performance of a process tool but is otherwise not suitable for use in production. An example of a test substrate is a bare wafer onto which the ARL is deposited. A silicon wafer having a crystalline structure that is not suitable for fabricating semiconductor devices is commonly used as a test substrate. Another example of a test substrate is a lithograph mask that has been fabricated using test grade glass instead of production grade glass. Generally test substrates are less expensive than production grade substrates.

The reflectivity of the ARL is measured at a desired wavelength (e.g., the wavelength used for exposing the photo-resist). The thickness, refractive index, and/or extinction coefficient of the ARL are adjusted to minimize reflectivity at the desired wavelength (e.g., during a lithographic process). For example, the refractive index and/or the extinction coefficient of a material may be adjusted by changing the material composition of the ARL. The thickness may be adjusted by controlling the deposition time for the ARL. The ARL is then applied to another test substrate to confirm suppression of the reflected light at the desired wavelength. Several iterations may be required.

Unfortunately, the manufacturing process for the production substrates is generally stopped while running the test substrates through the process and adjusting the process. Moreover, the performance of the ARL on the test substrate may not reflect the performance of the ARL on the production substrates. Complex experiments and calculations may be necessary to match the test substrate results to the production substrate performance.

Another method for measuring properties of the ARL on the substrate includes measuring reflected light at the desired wavelength from a light beam having a small spot size directed to regions between dies on a production substrate (also known as scribe lines, streets or alleys). The scribe lines are selected because they are regions where there are no features or underlying structure between the dies.

The features in the dies can add noise to the measurements. Unfortunately, measuring the properties of the ARL using this method requires aligning the substrate to place the small spot size into the streets between the dies. Alignment requires fine focus position control and is generally difficult and/or time consuming. Moreover, the ARL in the streets and alleys may not be representative of the ARL over the dies.

SUMMARY OF THE INVENTION

An embodiment of a metrology apparatus includes an emitter configured to emit an incident light beam at a production substrate on which an ARL has been deposited. The metrology apparatus further includes a receiver configured to receive a reflected light beam from the substrate and a spectrometer configured to determine a digital signal representing an intensity of a wavelength within the reflected light beam. The metrology apparatus also includes a processor configured to determine a spectrum of the reflected light beam from the digital signal. The processor is further configured to select a suppression band based on an expected wavelength representative of a portion of the ARL and determine a property of the ARL based on a portion of the spectrum in the suppression band of the spectrum.

In some embodiments, measurements are performed "on the fly," i.e., without stopping movement of the substrate, without positioning or aligning the substrate. Further, measurements may be performed without focusing on the substrate surface. A property of the ARL may include, but is not limited to, a thickness, a reflectivity, a refractive index, and/or an extension coefficient.

The effective wavelength of the ARL on the production substrate may be measured directly and provided to a process tool configured to deposit a photo-resist layer on the production substrate and/or expose the photo-resist layer. The effective wavelength may be used by the process tool to adjust a property of the photo-resist layer and/or the wavelength of the light used to expose the photo-resist layer and/or a property of an exposure process.

A property of the ARL on a production substrate may be measured directly while the substrate is being processed within a process tool. The property (e.g., measurement information of the property) of the ARL may be used to control application of the ARL by the process tool to the production substrate. In some embodiments, a property determination (e.g., measurement information of the property) of the ARL is provided to a process tool that has processed the production substrate. The property determination may be used to control processing of a subsequent production substrate by the process tool.

Further, the diameter of the incident light beam may be greater than 10 millimeters. The suppression band of the ARL may be less than 350 nanometers. Moreover, the emitter may be configured to emit the incident light beam for less than one second. In some examples, a mount may position the emitter over a substrate path or attach the emitter and the receiver to a process tool.

Various embodiments of the invention include a metrology method comprising emitting an incident light beam onto a production substrate including an ARL, receiving a reflected light beam, determining a spectrum of the reflected light beam, selecting a suppression band based on an expected wavelength representative of a portion of the ARL, and determining a property of the ARL based on a portion of the spectrum in the selected suppression band.

Various embodiments of the method include a metrology method comprising emitting a multiple wavelength radiation beam onto an area of a production substrate including an ARL, detecting intensities and wavelengths of a reflected radiation beam, analyzing the intensities and wavelengths to determine a spectrum of the intensities at respective wavelengths, transforming the spectrum of the intensities into a frequency spectrum, selecting a suppression band based on an expected wavelength representative of a portion of the ARL, and determining a property of the ARL based on a portion of the spectrum in the selected suppression band.

DETAILED DESCRIPTION

Figure 1A:
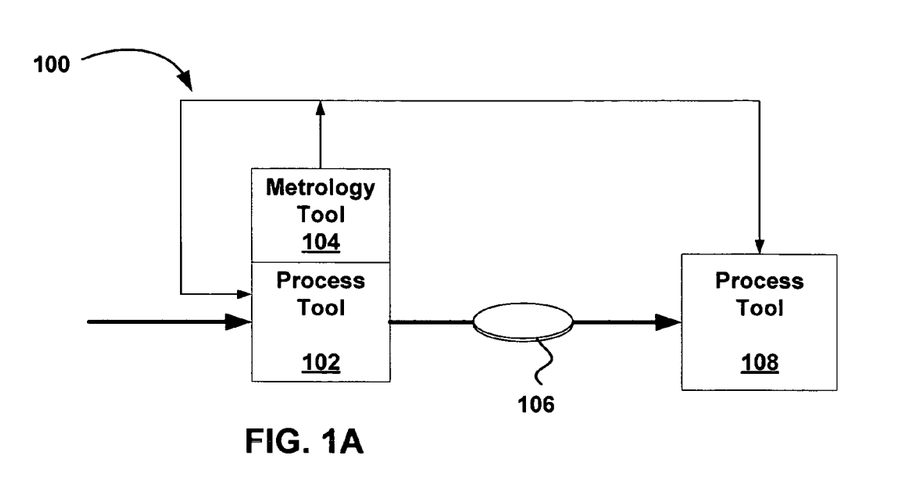
FIG. 1A is a block diagram illustrating an environment for processing a production substrate, according to some embodiments.

FIG. 1A is a block diagram illustrating an environment 100 for processing a production substrate 106, according to some embodiments. The processing environment 100 includes a process tool 102, a metrology tool 104, and a process tool 108. The production substrate 106 is a body of material upon which components, circuits, and/or devices are formed, etched, mounted, or otherwise placed, and from which one or more products may be fabricated. Examples of the production substrate 106 include a silicon wafer, a photolithographic glass, a gallium arsenide wafer, a germanium wafer, a silicon germanium wafer, etc. Examples of product include a semiconductor device, a microprocessor, a photolithographic mask, a disk drive read/write head, magnetic memory, a photo sensitive element, a light emitting element, a micro mechanical device, and so forth.

A typical production substrate 106 may include many semiconductor devices arranged as an array of dies. Each die may include multiple layers (e.g., a source layer, a drain layer, a capacitor layer, a resistor layer, a gate layer, a contact pad layer, a conductor layer, and a trench layer). Information regarding semiconductor manufacturing processes is described in greater detail in U.S. patent application Ser. No. 11/717,327 filed on Mar. 12, 2007 entitled "Method and Apparatus for Process Control With In-Die Metrology," which is hereby incorporated herein by reference.

Some layers of material on the production substrate 106 have optical properties. Optical properties of the production substrate 106 describe interaction of electromagnetic radiation with the semiconductor material as well as features in the semiconductor material. Examples of optical properties include a refractive index, an absorption coefficient, an extinction coefficient, and a reflectivity.

The refractive index of a material is a measure of how much the speed of light is reduced inside a material compared to the speed of light in vacuum. The speed of light such as the light beam in a material such as an ARL on the production substrate 106 depends on the wavelength of the light. For example, in the ARL, the refractive index is the ratio of the speed of an incident light beam in a vacuum to the phase velocity of the incident light beam within the ARL, as measured at the wavelength of the incident light beam. The refractive index of vacuum is 1.0. The refractive index of various materials is generally greater than 1.0.

The absorption coefficient of a material such as the ARL in the production substrate 106 is a measure of the absorption of light. (i.e., the absorption of the incident light beam by the ARL). The intensity of the incident light beam decreases as it propagates through the ARL. The decrease of intensity may be calculated based on an exponential function of the distance of the propagation and the absorption coefficient. The absorption coefficient may range from 0 (no absorption) to infinity (total absorption).

The extinction coefficient of a material, such as the ARL of the production substrate 106, is a measure of both scattering and absorption of the incident light beam by the ARL. The decrease of the intensity of the incident light beam as it propagates through the ARL may be calculated based on an exponential function of the distance of the propagation and the extinction coefficient. The extinction coefficient has a range of 0 (no extinction) to infinity (total extinction). Both the extinction coefficient and the absorption coefficient depend on the wavelength of the incident light beam. For example, the extinction coefficient is directly proportional to a product of the wavelength of the incident light beam and the absorption coefficient, whereas the absorption coefficient is directly proportional to the extinction coefficient divided by the wavelength of the incident light beam.

Reflectivity is the fraction of incident light that is reflected by one or more layers within the production substrate 106. In one example, an emitter/receiver receives a reflected light beam reflected from the production substrate 106. A spectrometer may determine the reflectivity by determining the ratio of reflected spectral intensity to the incident spectral intensity (i.e., the spectral intensity of the reflected light beam to the spectral intensity of the incident light beam). The incident light beam, reflected light beam, emitter/receiver, and spectrometer are further discussed in FIG. 2.

A process tool is manufacturing equipment that is configured to add, remove, or modify material of the production substrate 106. In one example, the process tool alters (i.e., adds, removes, or modifies) material to change physical properties of the production substrate 106. The process tool may add, remove, and/or modify the material selectively or in bulk. In a further example, the process tool 102 is comprises thin film deposition equipment configured to deposit a thin film (e.g., an ARL) onto a production substrate 106.

The process tool 102 and the process tool 108 may or may not perform similar operations on the production substrate 106. In one example, the process tool 102 is a tool configured to perform a process for applying an ARL to the production substrate 106. The process tool 108 may be configured to perform a process on the production substrate 106 including, but not limited to, applying a photo-resist to the substrate and/or exposing the photo-resist.

For clarity, only one process tool 102 and one process tool 108 are illustrated in FIG. 1A; however, a person of ordinary skill in the art will appreciate that multiple process tools 102 and/or multiple process tools 108 may be used to perform various processes on the production substrate 106.

The metrology tool 104 may be used to measure one or more production substrates 106. In some embodiments, the measurement information of a production substrate 106 is used for monitoring the process tool 102. The measurement information may also be used for adjusting the process tool 102 and/or the process tool 108.

In various embodiments, the metrology tool 104 is disposed within an environmental enclosure of the process tool 102 (e.g., adjacent a loading lock of the process tool 102, a port in a process chamber, or over a cooling station). Alternatively, the metrology tool 104 may be disposed within a process chamber of the process tool 102. In other embodiments, the metrology tool 104 may be disposed within or adjacent to an environmental front end module (EFEM). The position of the metrology tool 104 may be selected to measure the production substrate 106 on the fly, without aligning, focusing, or adjusting the X, Y, or Z positions of the production substrate 106.

In some embodiments, the metrology tool 104 is configured to measure a property (i.e., a thickness or optical property) of an ARL on the production substrate 106 in the process tool 102 during deposition and/or modification of the ARL on the production substrate 106. The metrology tool 104 may also be configured to perform measurements on the production substrate 106 while the production substrate 106 is in situ within the process tool 102. In various embodiments, the metrology tool 104 may be configured to perform measurements on the production substrate 106 as the production substrate 106 is being loaded into and/or unloaded from the process tool 102.

Measurement information that is based on the property of the ARL may be provided to the process tool 102 and/or the process tool 108. In one example, the measurement information may be used to adjust the process tool 102. In various embodiments, the process tool 102 may use the measurement information to adjust the thickness, refractive index, and/or extinction coefficient of the ARL on the production substrate 106 being measured. For example, the process tool 102 may receive real time measurements of a thickness of the ARL on the production substrate 106 from the metrology tool 104 during material deposition, and stop the deposition in response to the real time measurements upon achieving a desired thickness of the ARL.

In some embodiments, the metrology tool 104 is configured to measure a property of the ARL on the production substrate 106 after the ARL has been deposited by the process tool 102. The process tool 102 may use the measurement information of the ARL on a production substrate 106 to adjust the application of the ARL of a subsequent production substrate 106. Moreover, the process tool 108 may use the measurement information to adjust a subsequent process to be applied to the production substrate 106. For example, the process tool 108 may use the measurement information to adjust a property of the photo-resist, e.g., the thickness, refractive index, and/or extinction coefficient of the photo-resist. In some embodiments, the process tool 108 may use the measured property to adjust a wavelength of light used to expose the photo-resist.

For example, the process tool 108 may receive an effective wavelength for the ARL on the production substrate 106 from the metrology tool 104 after the ARL is deposited by the process tool 102 and use the effective wavelength to adjust the wavelength of the light used for exposing a photo-resist layer subsequently disposed over the ARL. The effective wavelength is a wavelength at which an intensity of a light beam reflected from the ARL is a local minimum within a selected wavelength band. Thus, the feeding forward of measurement information may be used to compensate for a defect due to the process tool 102 rather than scrapping the production substrate 106 because of the defect. In various embodiments, the process tool 108 may adjust an exposure duration and/or an intensity of a light used for exposing the photo-resist layer based on a refractive index, extinction coefficient, and/or a reflectivity received from the metrology tool 104.

Figure 1B:
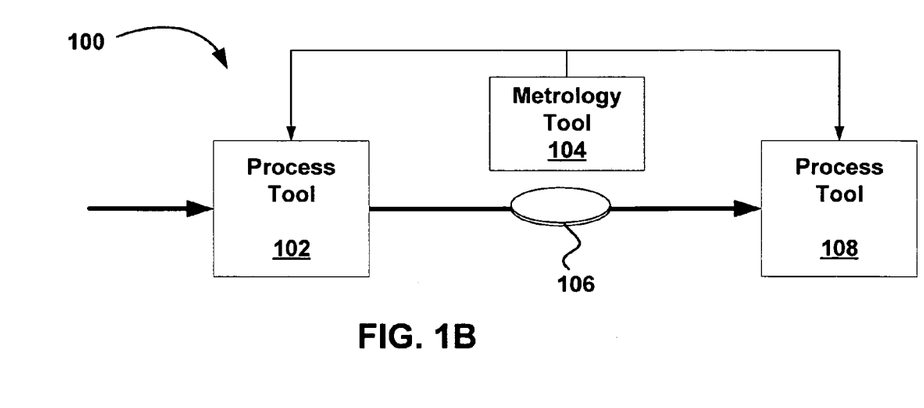
FIG. 1B is a block diagram illustrating an alternative embodiment of an environment for processing a production substrate.

FIG. 1B is a block diagram illustrating an alternative embodiment of an environment 100 for processing a production substrate 106. FIG. 1B differs from FIG. 1A in that the metrology tool 104 is disposed between the process tool 102 and the process tool 108 along a path of the production substrate 106. In some embodiments, the metrology tool 104 is configured to measure the production substrate 106 while the production substrate 106 is being transported between the process tool 102 and the process tool 108. As discussed above, the measurement information may be used to adjust the process tool 102 and/or the process tool 108.

Figure 2:
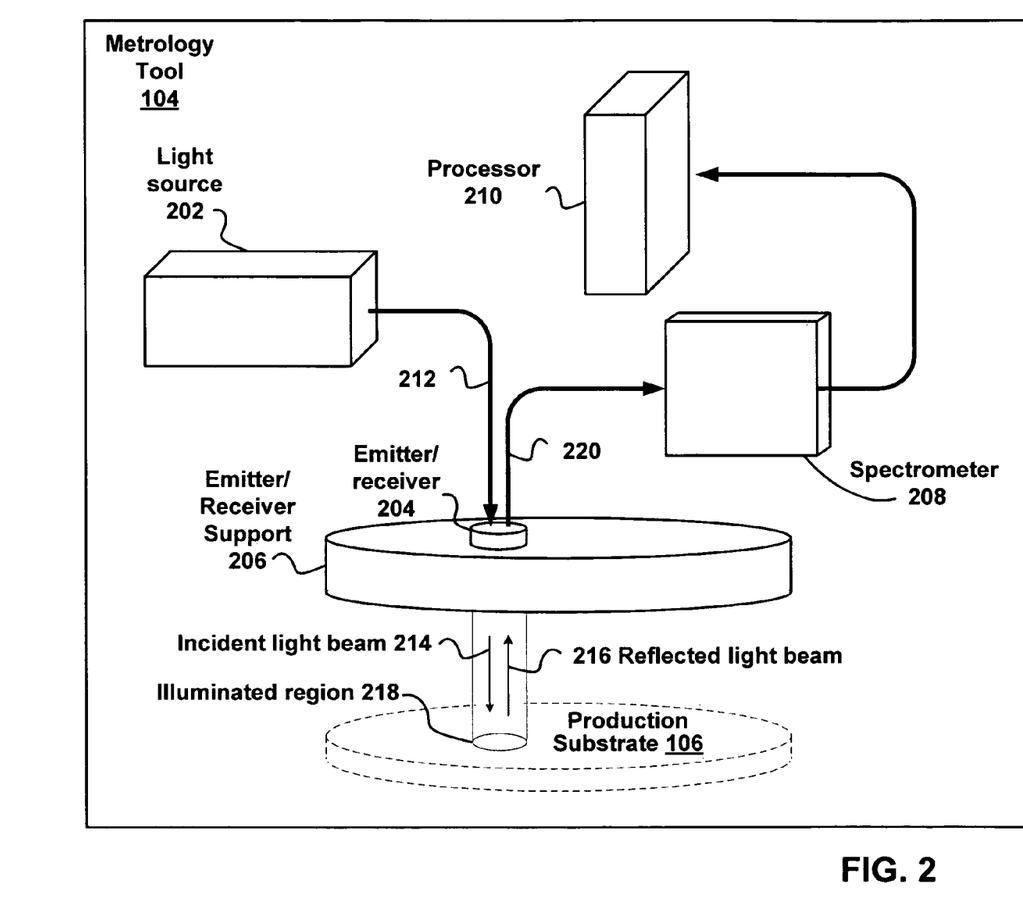
FIG. 2 is a diagram illustrating details of the metrology tool of FIG. 1A and/or FIG. 1B, according to one embodiment.

FIG. 2 is a block diagram illustrating details of the metrology tool 104 of FIG. 1A and/or FIG. 1B, according to one embodiment. The metrology tool 104 includes a light source 202, an emitter/receiver 204, an emitter/receiver support 206, an optional spectrometer 208, and an optional processor 210. The light source 202 is configured to produce a light beam. The light source 202 may be coupled to the emitter/receiver 204 using an optional fiber optic conductor 212. In various embodiments, the light source 202 may include an incandescent light, a light emitting diode (LED), a laser, etc.

The light source 202 may be configured to produce an incident light beam 214 as monochromatic light or as light in one or more selected bands of the visible, infrared, and/or ultraviolet light spectrum. The incident light beam 214 may illuminate a region 218 on the production substrate 106, and may be reflected from the production substrate 106, becoming a reflected light beam 216. The emitter/receiver 204 may subsequently receive the reflected light beam 216.

The incident light beam 214 may include polarized light, non-polarized light, or a combination of polarized and non-polarized light. The light source 202 may be configured to emit a beam in the electromagnetic spectrum outside the light spectrum. Further, in various embodiments, the light source 202 is configured to provide a continuous incident light beam 214, pulsed incident light beam 214, an on demand incident light beam 214, and so forth.

The emitter/receiver 204 is configured to emit the incident light beam 214 at the production substrate 106 and receive the reflected light beam 216 from the production substrate 106. In some embodiments, the emitter/receiver 204 may be combined with the light source 202, and the fiber optic conductor 212 may be omitted. The emitter/receiver 204 may include optical components configured to collimate and/or focus the incident light beam 214 (e.g., at a plane of the production substrate 106).

The emitter/receiver support 206 is a structure configured to position the emitter/receiver 204 proximate the production substrate 106. In various embodiments, the emitter/receiver support 206 couples the emitter/receiver 204 to a chamber lid, a load lock lid, a port, a chamber wall, an enclosure component, a wall of an EFEM, and/or other process tool 102 component. In one example, the emitter/receiver support 206 is configured to dispose the emitter/receiver 204 in a position for emitting the incident light beam 214 at the production substrate 106.

In some embodiments, the emitter/receiver support 206 is transparent or includes a transparent portion (not illustrated) and the emitter/receiver 204 is mounted over the emitter/receiver support 206 and configured to emit the incident light beam 214 through the transparent portion (e.g., the incident light beam 214 is emitted through the emitter/receiver support 206 as if through a window). Alternatively, the emitter/receiver 204 is mounted inside the process tool 102.

While only one emitter/receiver 204 is illustrated in the emitter/receiver support 206 of FIG. 2, it is contemplated that a plurality of emitter/receivers 204 may be disposed in the emitter/receiver support 206. Multiple emitter/receivers 204 disposed in the emitter/receiver support 206 may provide simultaneous measurements of multiple sites on the production substrate 106. In some embodiments, simultaneous measurements enhances throughput. Further, the emitter/receiver 204 may be configured to emit the incident light beam 214 normal to the production substrate 106 which may render the incident light beam 214 less sensitive to effects of an uneven surface in the production substrate 106.

While the emitter and the receiver of the emitter/receiver 204 are illustrated as combined, the emitter and receiver may be separate components. In one example, the emitter and receiver may be disposed in a separate location on the emitter/receiver support 206 or on separate emitter/receiver supports 206.

The metrology tool 104 may be configured to illuminate the production substrate 106 in many locations. In one example, the production substrate 106 is illuminated inside the metrology tool 104. Alternatively, the metrology tool 104 may be positioned in order to illuminate the production substrate within the process tool 102. Optionally, the metrology tool 104 may be configured to illuminate the production substrate 106 with the incident light beam 214 and receive the reflected light beam 216 while the production substrate 106 is in transit on a path between the process tool 102 and process tool 108. In some embodiments, the metrology tool 104 may be combined with the process tool 102 and configured to illuminate the production substrate 106 while the production substrate 106 is inside the process tool 102.

The spectrometer 208 is configured to receive the reflected light beam 216 from the emitter/receiver 204 via an optional fiber optic conductor 220 and convert the reflected light beam 216 to digital signals having a format of intensities as a function of wavelength. In some embodiments, the spectrometer 208 is also configured to determine incident light beam information regarding the incident light beam 214 (e.g., the spectral intensity of the incident light beam 214). The spectrometer may be combined with the emitter/receiver 204. Optionally, the spectrometer 208 includes an onboard processor configured to determine the spectrum of the reflected light beam 216 and provide the spectrum to the processor 210.

In some embodiments, the spectrometer 208 is combined with a spectrum analyzer (not illustrated) and configured to determine a spectrum of the reflected light beam 216. The spectrum analyzer may determine the spectrum using software and/or hardware similar to the processor 210. For example, the spectrum analyzer may use a Fourier transform, a chirplet transform, a Hartley transform, a Z-transform, or a constant-Q transform to determine the spectrum of the reflected light beam 216. In some embodiments, the spectrometer 208 may also receive the incident light beam 214. In this embodiment, the processor 210 receives the spectrum data from the spectrum analyzer. In some embodiments the processor 210, the spectrometer 208, and the spectrum analyzer may be combined.

The processor 210 is configured to receive the digital signals from the spectrometer 208 and determine a spectrum of the reflected light beam 216 based on the digital signals. The processor 210 may use a Fourier transform and/or various other transforms (e.g., a chirplet transform, a Hartley transform, a Z-transform, a constant-Q transform, etc.) to determine the spectrum of the reflected light beam 216. In various embodiments, the processor 210 uses hardware, firmware, and/or software to determine the spectrum. For example, the processor 210 may include a digital signal processor (DSP) configured to determine the spectrum of the reflected light beam 216.

In some embodiments, the processor 210 may also receive digital signals representing intensities and wavelengths of the incident light beam 214 and determine the spectrum of the incident light beam 214. In some embodiments the processor 210 and the spectrometer 208 may be combined. The processor 210 may be further configured to use the digital signals (i.e., the digital signals) received from the spectrometer 208 to determine a property of at least one layer of material on the production substrate 106.

Figure 3:
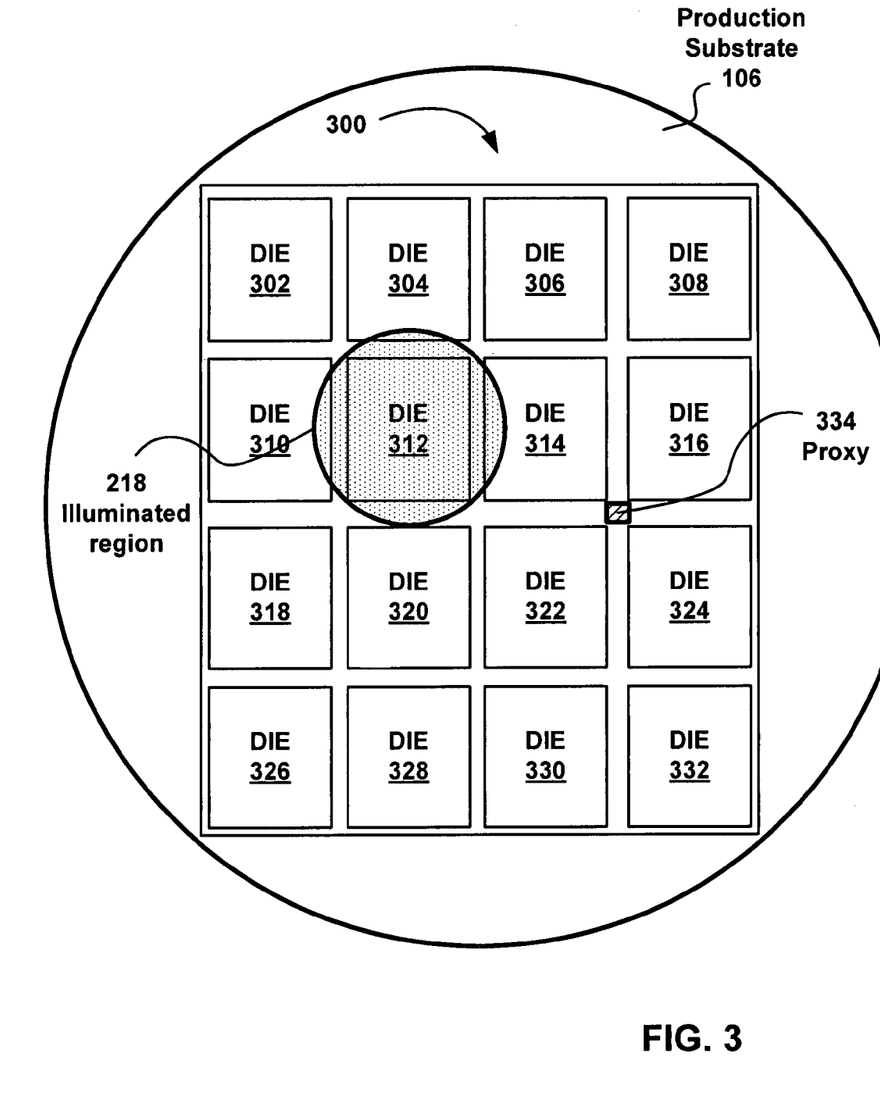
FIG. 3 is a top plan view of an exemplary production substrate.

FIG. 3 is a top plan view of an exemplary production substrate 106. The surface of the production substrate 106 is illustrated as including an array of dies 300, which includes dies 302-332. In various embodiments, the dies 302-332 may be identical, different, or comprise one or more repeating patterns of sub-arrays or any other arrangement. The illuminated region 218 is illustrated as encompassing an exemplary die 312. In various embodiments, the illuminated region 218 may encompass the entire die 312, a portion of the die 312, another die of the array 300, or multiple dies (e.g., die 314, 316, 322, and 324). The production substrate 106 may be illuminated by the incident light beam 214 without damaging or modifying the portion of the production substrate 106 in the illuminated region 218. In some embodiments, a proxy 334 is included on the surface of the production substrate 106 (e.g., between the dies in streets and/or alleys) for monitoring processing performed by the process tool 102.

Figure 4:
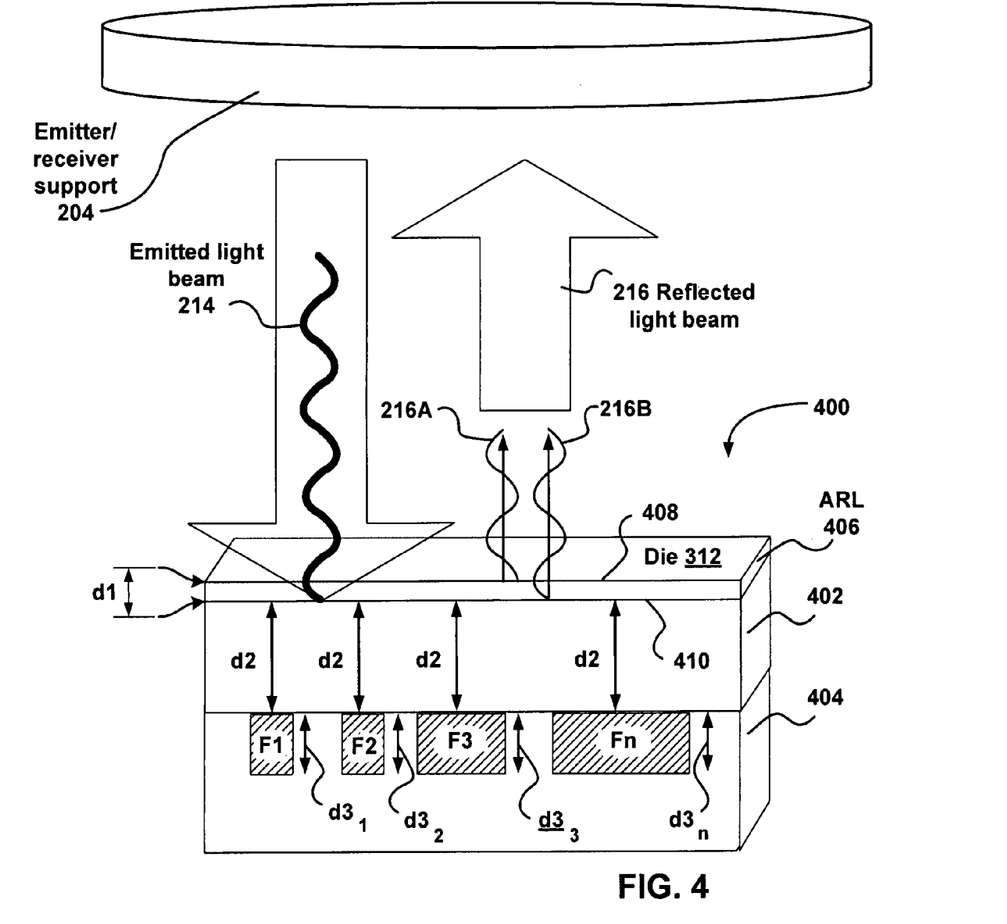
FIG. 4 is a perspective view of an exemplary cross-section of a die in the production substrate of FIG. 3, according to one embodiment.

FIG. 4 is a perspective view of an exemplary cross-section 400 of a die 312 in the production substrate 106 of FIG. 3, according to one embodiment. The die 312 includes an ARL 406 comprising a top surface 408 and a bottom surface 410. The ARL 406 may comprise a combination of one or more materials designed to suppress a range of light wavelengths. For example, a material known as Oxinitride, which is a composition of Silicon Oxide (SiO2) and Silicon Nitride (Si3N4), is commonly used in an ARL layer. The thickness and/or proportions of the Silicon Oxide and the Silicon Nitride in the ARL layer may be adjusted to control reflectivity properties of the ARL at various wavelengths.

The ARL 406 illustrated in FIG. 4 has a thickness of d1. The thickness d1 combines with the refractive index and extinction coefficient of the ARL to determine an effective wavelength of the ARL. In some embodiments, the thickness d1 of the ARL is less than about 350 angstroms.

The incident light beam 214 illuminates the die 312. The reflected light beam 216A is reflected light from the top surface 408 and the reflected light beam 216B is reflected light from the bottom surface 410. The combined reflected light beams 216A and 216B form the reflected light beam 216 of FIG. 2.

When the reflected light beam 216A is 180 degrees out of phase with the reflected light beam 216B (i.e., destructive interference) the intensity of the reflected light beam 216 is equal to the difference of the magnitude between the reflected light beam 216A and 216B. In general, when the thickness d1 is about one quarter of the wavelength of the incident light beam 214, the reflected light beam 216A is 180 degrees out of phase with the reflected light beam 216B. When the magnitude of the reflected light beam 216A is equal to the reflected light beam 216B, the destructive interference results in total cancellation and the intensity of the reflected light beam 216 is zero. The intensity of the reflected light beam 216B may be adjusted to match the intensity of the reflected light beam 216A using the extinction coefficient and the refractive index of the ARL.

The die 312 includes layers 402 and 404 disposed below the ARL 406. In various embodiments, properties of the layers 402 include a thickness such as a thickness d2, a refractive index, and an extinction coefficient. The layer 404 includes one or more production features F1, F2, F3, ... Fn (F1-Fn). A production feature (i.e., a feature) is a device or an element of a device within a production substrate 106. In one example a feature is a geometric region within a layer such as, but not limited to, a trench, a conductor, a wire, a resistor, a "P" region of a transistor, and an "N" region of a transistor. A person of ordinary skill in the art will understand that the layer 404 may include one or more (likely thousands or millions) of production features F1-Fn within the illuminated region 218.

In some embodiments, the production features F1-Fn may include a plurality of features having a common property. For example, the production features F1-Fn may include some number of filled trenches, all placed in the layer 404 within the illuminated region 218 of the production substrate 106 and having approximately the same thicknesses. In various embodiments, each production feature F1-Fn may have certain properties, such as thicknesses $d3_1$, $d3_2$, $d3_3$, ... $d3_n$ ($d3_1$-$d3_n$), respectively. While $d3_1$-$d3_n$ are used in FIG. 4A to represent thicknesses of production features F1-Fn respectively, a practitioner with ordinary skill in the art will understand that $d3_1$-$d3_n$ may also represent properties other than thickness, including but not limited to the refractive index and the extinction coefficient.

The layer 402 may include a bulk layer of material disposed above the layer 404 of production features F1-Fn. The layer 402 may have homogeneous properties, such as thickness d2, approximately constant throughout the layer 402. The layer 402 also may have different properties, such as thicknesses d2, immediately above the different production features F1-Fn. While the thickness d2 is illustrated as uniform above F1-Fn, a practitioner of ordinary skill in the art will understand that the thickness d2 may vary from production feature to production feature. Furthermore, while d2 is used illustratively to represent the thicknesses of the layer 402 above the production features F1-Fn, a practitioner with ordinary skill in the art will again understand that d2 may also represent properties other than thickness, including but not limited to the refractive index and the extinction coefficient. In some embodiments the ARL suppresses light reflected from layers below the ARL, e.g., the layers 402 and 404.

Figure 5:
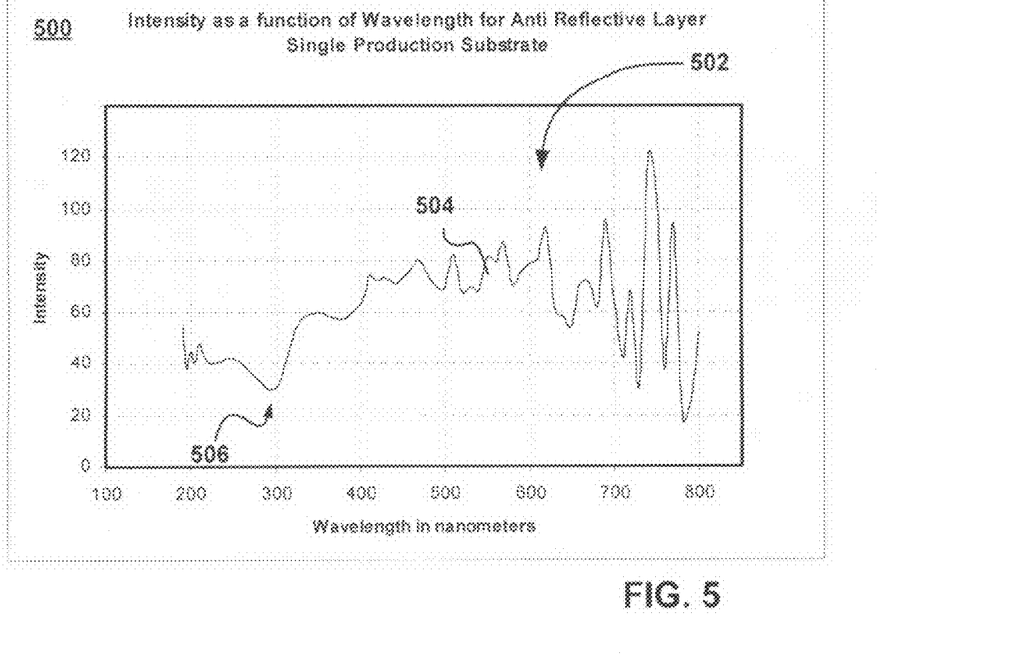
FIG. 5 illustrates a graph of an exemplary spectrum of the reflected light beam reflected from the production substrate die, according to one embodiment.

FIG. 5 illustrates a graph 500 of an exemplary spectrum 502 of the reflected light beam 216 reflected by the production substrate 106, according to one embodiment. A horizontal axis of the graph represents the wavelength of the reflected light beam 216 expressed in units of nanometers (nm). A vertical axis of the graph represents the intensity of the reflected light beam 216 expressed in arbitrary units. The spectrum 502 represents intensities of the reflected light beam 216 as a function of the wavelength Properties of the production substrate 106 may be determined from the spectrum 502 of the reflected light beam 216. For wavelengths between about 250 nm and about 400 nm, the ARL suppresses reflected light from layers below the ARL. The range of wavelengths for which the ARL suppresses reflected light from below the ARL may be referred to as a suppression band. The suppression band also includes a wavelength region in which an intensity of the reflected light beam 216 reflected from the surface of the production substrate 106 is minimized by the ARL.

As illustrated in FIG. 5, the suppression band ranges from about 250 nm to about 400 nm. The effective wavelength of the ARL may be determined from a local minimum within the suppression band. An effective wavelength 506 is illustrated at about 280 nm. In some embodiments, the ARL thickness d1 is about one quarter of the effective wavelength 506 or about 70 nm. Additional properties such as layer thickness d1, refractive index n, and extinction coefficient k may also be determined using the spectrum within the suppression band as described elsewhere in this specification.

At wavelengths in the range of about 400 nm to 800 nm, the production features (e.g., F1-Fn) in layers below the ARL (e.g., layers 402 and 404) contribute to the spectrum 502. The contributions to the spectrum 502 include multiple peaks (e.g., a peak 504) representing properties of various layers below the ARL. The range of wavelengths for which the ARL transmits reflected light from below the ARL may be referred to as the transmission band. As illustrated in FIG. 5, the transmission band ranges from about 400 nm to about 800 nm.

Figure 6:
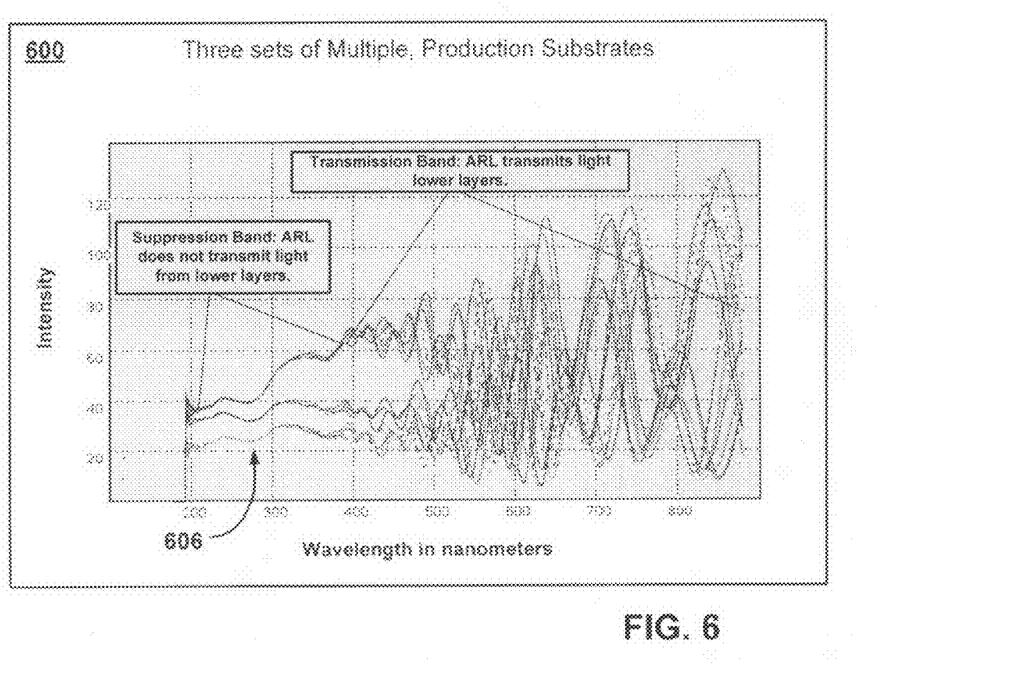
FIG. 6 illustrates a graph of exemplary spectra of multiple production substrates, according to one embodiment.

FIG. 6 illustrates a graph 600 of exemplary spectra for multiple production substrates, according to one embodiment. FIG. 6 differs from FIG. 5 in that the graph 600 illustrates three groups of spectra for multiple production substrates 106, instead of the single spectrum 502 represented in FIG. 5. A horizontal axis of the graph 600 represents the wavelength of the reflected light beam 216 expressed in units of nanometers. A vertical axis of the graph represents the intensity of the reflected light beam 216 expressed in arbitrary units. Each spectrum in the graph 600 illustrates the intensity of the reflected light beam 216 from a respective production substrate 106 as a function of the wavelength. As illustrated in FIG. 5, the transmission band for the spectra in the graph 600 ranges from about 350 nm to about 800 nm. The suppression band for the graph 600 ranges from about 225 nm to about 350 nm. The effective wavelength 606 for the ARL for the production substrates 106 is about 275 nm.

The number and distribution of the peaks in the transmission band of the graph 600 indicates a variety of features and properties for the features in the production substrates 106. The uniformity of the spectra in the suppression band illustrates suppression of reflections from the features below the ARL of the production substrates 106

Figure 7:
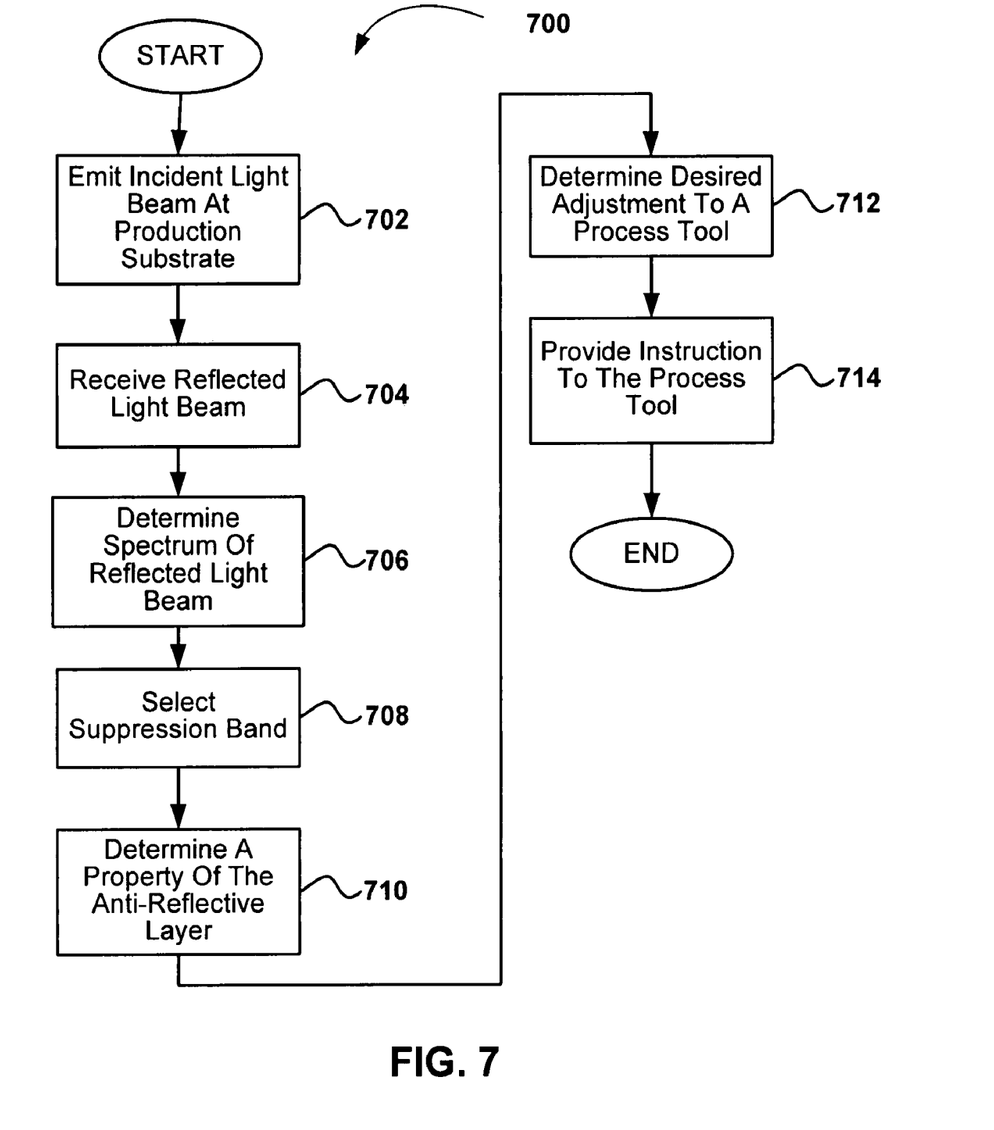
FIG. 7 is a flow diagram of an exemplary metrology tool operation method, according to one embodiment.

FIG. 7 is a flow diagram of an exemplary metrology tool operation method 700, according to one embodiment. The metrology tool operation method 700 may be used to measure properties of an ARL on a substrate (e.g., the production substrate 106) using a metrology tool (e.g., the metrology tool 104). The measurements may be used for providing adjustments to the process tool 102.

In step 702, an incident light beam 214 is emitted by an emitter/receiver 204 at a production substrate 106 that includes an ARL. The incident light beam 214 is configured to illuminate the illumination region 218 on the production substrate 106. The incident light beam 214 is reflected from the production substrate 106 as the reflected light beam 216.

In step 704, the emitter/receiver 204 receives the reflected light beam 216. Optionally, the emitter/receiver 204 also receives the incident light beam 214 for comparison with the reflected light beam 216.

In step 706, a spectrum of the reflected light beam 216 is determined. In various embodiments, the spectrum is determined using a spectrometer 208, a processor 210, or a spectrum analyzer coupled to the spectrometer 208.

In step 708, a suppression band is selected. The selection of the suppression band is based on an expected wavelength, representative of a portion of the ARL (e.g., the illuminated region 218). In some embodiments, an effective wavelength (e.g., the effective wavelength 506) is estimated. Alternatively, the expected wavelength may be based on the effective wavelength 506. The suppression band may be selected to include the effective wavelength and/or exclude reflected light from layers below the ARL. In some embodiments, the processor 210 selects the suppression band. Alternatively, the processor 210 is configured to determine the expected wavelength and/or select the suppression band based on an analysis of the spectrum of the reflected light beam 216. Optionally, a transmission band is selected and the spectrum in the transmission band is analyzed to determine properties of production features in layers below the ARL.

In step 710, a property of the ARL is determined (e.g., measured). In various embodiments, the property of the ARL includes the thickness, reflectivity, refractive index, extinction coefficient, and/or effective wavelength for the ARL. The processor 210 may be configured to determine the property (i.e., measurement information) of the ARL based on a portion of the spectrum in the suppression band. The portion of the spectrum in the suppression band may include the entire suppression band and/or a part of the suppression band. For example, the portion of the spectrum may include a band with a minimum intensity within the suppression band. Information regarding determining a property of a substrate layer from a spectrum is described in greater detail in U.S. patent application Ser. No. 11/717,327 filed on Mar. 12, 2007 entitled "Method and Apparatus for Process Control With In-Die Metrology."

In an optional step 712, a desired adjustment to a process tool is determined. In various embodiments, equations and/or algorithms may be used to determine the desired adjustment based on property determination (i.e., measurement information) discussed in steps 702-710. For example, a spectrum may be predicted for the reflected light beam 216 based the thickness $d_1$, refractive index n, and extinction coefficient k using Equation 1. Equation 1 represents the reflectance model of a single layer on a substrate as a function of wavelength $\lambda$ and may be used to construct a predicted spectrum $R(\lambda)$.

$$R(\lambda) = \frac{[r_{01}^2 + r_{12}^2 + 2r_{01}r_{12}\cos(2\varphi_1)]}{[1 + r_{01}^2 + r_{12}^2 + 2r_{01}r_{12}\cos(2\varphi_1)]} \quad \text{Equation 1}$$

where $$\varphi_m = \frac{2\Pi N_m d_m}{\lambda}$$

$$r_{ij} = \frac{N_i - N_j}{N_i + N_j}$$

$$N_i = n_i - jk_i$$

where $R(\lambda)$ is the intensity of the reflected light beam 216, $n_1$ is the refractive index of the ARL, $k_1$ is the extinction coefficient of the ARL, and d1 is the thickness of the ARL. Further, $n_0$ is the refractive index for the material over the ARL (e.g., air, vacuum, or photo-resist). Likewise, $k_0$ is the extinction coefficient for the material over the ARL. Moreover, $n_2$ and $k_2$ are the refractive index and extinction coefficient respectively for the substrate below the ARL.

In some embodiments, the accuracy of Equation 1 may be improved by using additional equations that may more accurately relate the refractive index n and extinction coefficient k to the wavelength $\lambda$ of the reflected light beam 216. For example, as a first approximation the refractive index n and the extinction coefficient k may be treated as constants. Both n and k may vary as a function of $\lambda$. In some embodiments, n and k relation may be obtained using the Kramers-Kronig relation as expressed in an Hilbert Transform (HT) form as set forth in Equation 2:

$$n(e) = 1/\pi PV \int_{-\infty}^{+\infty} \frac{k(E)}{E-e} dE \quad \text{Equation 2}$$

where $e=1240/\lambda$ and

PV=Cauchy principal value

E is the integral argument

A person of ordinary skill in the art will appreciate that the relationship between the parameters n, k, and λ as set forth in Equation 2 may be applied to Equation 1 to compute a predicted spectrum R(λ).

In an optional step 714, an instruction is provided to the process tool. In various embodiments, the instruction is configured to adjust the thickness d1, the refractive index n, or the extinction coefficient k of the ARL. In some embodiments, the instruction is provided to a process tool to adjust the thickness d1, the refractive index n, or the extinction coefficient k of a different ARL on another production substrate 106. Moreover, the instruction may be provided to another process tool to control the deposition, removal, or modification of any material on the production substrate 106 to take into account the measured property of the ARL.

Equations 1 and 2 may be used to predict the effect on the predicted spectrum R(λ) resulting from a change to the parameter d1, n, and/or k to reduce reflectivity of the ARL at a desired wavelength λ. An example of the instruction to adjust the thickness d1 includes adjusting a deposition time in the process tool 102 for application of the ARL. An example of an instruction to adjust the refractive index n or extinction coefficient k of the ARL includes an instruction to adjust the mixture of the chemical components of the ARL.

Alternatively, the incident light beam 214 may be directed toward the production substrate 106 at a set of predefined incident angles. The reflected light beams 216 may be measured as described in the steps 702-710. Optionally, polarization information (i.e., ellipsometry) may be used to determine additional information using equations that are understood by persons skilled in the art, to represent additional physical relationships between the properties of the ARL.

Figure 8:
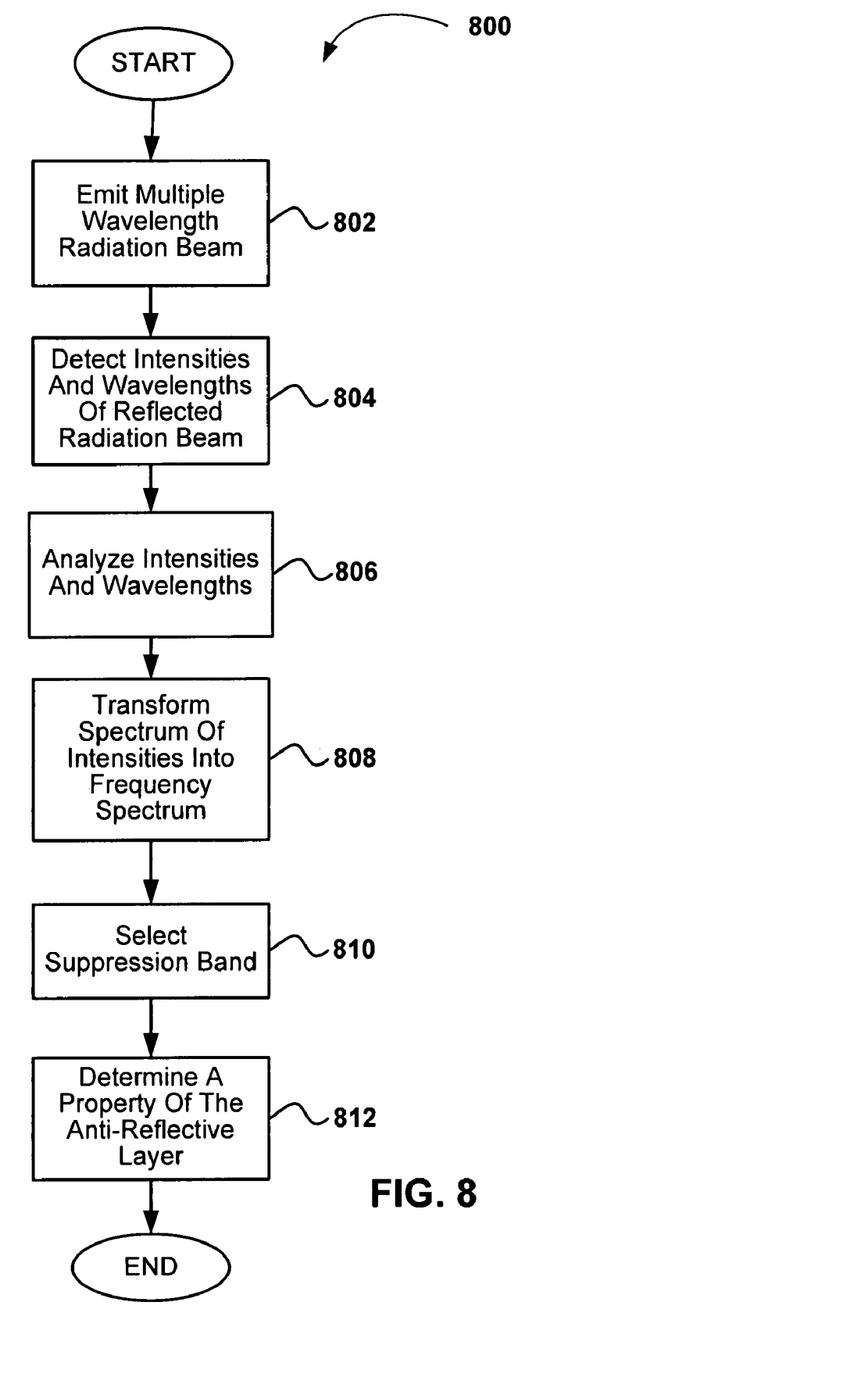
FIG. 8 is a flow diagram of an exemplary metrology tool operation method, according to one embodiment.

FIG. 8 is a flow diagram of an exemplary metrology tool operation method 800, according to one embodiment. The metrology tool operation method 800 may be used to measure properties of an ARL on a production substrate 106, using a metrology tool 104. The measurements may be used for providing adjustments to a process tool (e.g., the process tool 102 and/or the process tool 108).

In step 802, the incident light beam 214 is emitted by an emitter/receiver 204 onto the illuminated region 218 of the production substrate 106 including an ARL. The incident light beam 214 includes multiple wavelength radiation. In various embodiments, the multiple wavelength radiation beam includes infrared, visible, and/or ultraviolet light. The incident light beam 214 is reflected from the production substrate 106 as the reflected light beam 216.

In step 804, the emitter/receiver 204 detects the intensities and wavelengths of the reflected light beam 216. Optionally, the emitter/receiver 204 also receives the incident light beam 214 for comparison with the reflected light beam 216.

In step 806, the intensities and wavelengths detected in step 804 are analyzed. The analysis may be performed by a processor such as the processor 210 using a spectrometer such as the spectrometer 208, or another device configured to perform the analysis.

In step 808, the spectrum of the intensities analyzed in step 806 are transformed into a frequency spectrum (e.g., using the processor 210). Alternatively, a spectrum analyzer may be used to transform the spectrum of the intensities into a frequency spectrum.

In step 810, a suppression band is selected as discussed in the method 700. In step 812, a property of the ARL is determined, as discussed in the method 700.

Although the methods 700 and 800 are described as comprising various steps, the methods 700 and/or 800 may comprise fewer or more steps and still fall within the scope of various embodiments.

Several embodiments are specifically illustrated and/or described herein. However, it will be appreciated that modifications and variations are covered by the above teachings and within the scope of the appended claims without departing from the spirit and intended scope thereof. For example, the emitted light beam may be emitted at a moving substrate (e.g., translation and/or rotation). Alternatively, an emitter/receiver array may be configured for translation and/or rotation with respect to the substrate. The emitter/receiver may emit the light beam and/or receive the reflected light via fiber optics. The reflected light beam may be received from a moving substrate. Various embodiments of the invention include logic stored on computer readable media, the logic configured to perform methods of the invention.

The embodiments discussed herein are illustrative of the present invention. As these embodiments of the present invention are described with reference to illustrations, various modifications or adaptations of the methods and/or specific structures described may become apparent to a person with ordinary skill in the art. All such modifications, adaptations, or variations that rely upon the teachings of the present invention, and through which these teachings have advanced the art, are considered to be within the spirit and scope of the present invention. Hence, these descriptions and drawings should not be considered in a limiting sense, as it is understood that the present invention is in no way limited to only the embodiments illustrated.

What is claimed is:

1. A metrology method comprising:
   emitting an incident light beam onto a production substrate including an anti-reflective layer;
   receiving a reflected light beam;
   determining a spectrum of the reflected light beam;
   selecting a suppression band based on an expected wavelength representative of a portion of the anti-reflective layer; and
   determining a property of the anti-reflective layer based on a portion of the spectrum in the selected suppression band.

2. The method of claim 1, wherein the suppression band selection is further based on a suppression, by the anti-reflective layer, of at least some of the reflected light beam from a lower layer within the production substrate below the anti-reflective layer.

3. The method of claim 1, wherein determining the property of the anti-reflective layer comprises determining an effective wavelength within the reflected light beam and determining the property of the anti-reflective layer based on the effective wavelength.

4. The method of claim 1, wherein the property of the anti-reflective layer is a thickness, a reflectivity, a refractive index, or an extinction coefficient.

5. The method of claim 1, further comprising:
   applying a photosensitive emulsion over the anti-reflective layer after determining the property of the anti-reflective layer; and
   adjusting an exposure time for the photosensitive emulsion based on the property determination of the anti-reflective layer.

6. The method of claim 1, further comprising:
determining a desired adjustment to a process tool based on the property determination of the anti-reflective layer; and
providing an instruction to the process tool to make the desired adjustment.

7. The method of claim 1, further comprising:
selecting a transmission band outside the suppression band; and
determining a property of a lower layer below the anti-reflective layer based on the spectrum of the transmission band.

8. The method of claim 7, wherein the property of the lower layer below the anti-reflective layer is a thickness, a reflectivity, a refractive index, or an extinction coefficient.

9. The method of claim 1, wherein emitting the incident light beam onto a production substrate comprises emitting an incident light beam while moving the production substrate.

10. The method of claim 1, wherein the production substrate is a wafer.

11. The method of claim 1, wherein the production substrate is a lithographic mask.

12. The method of claim 1, wherein a suppression band is less than about 350 nanometers.

13. The method of claim 1, wherein emitting the incident light beam onto a production substrate comprises emitting the incident light beam for less than two hundred milliseconds.

14. A metrology tool comprising:
an emitter configured to emit an incident light beam at a production substrate including an anti-reflective layer;
a receiver configured to receive a reflected light beam from the production substrate;
a spectrometer configured to determine a digital signal representing an intensity of a wavelength within the reflected light beam; and
a processor configured to:
determine a spectrum of the reflected light beam from the digital signal;
select a suppression band based on an expected wavelength representative of a portion of the anti-reflective layer; and
determine a property of the anti-reflective layer based on a portion of the spectrum in the selected suppression band.

15. The metrology tool of claim 14, wherein a diameter of the incident light beam is greater than 10 millimeters.

16. The metrology tool of claim 14, the production substrate comprises a plurality of features in a lower layer below the anti-reflective layer.

17. The metrology tool of claim 14, wherein a suppression band of the anti-reflective layer is less than about 350 nanometers.

18. The metrology tool of claim 14, wherein the emitter is further configured to emit the incident light beam for less than one second.

19. The metrology tool of claim 14, further comprising a mount configured to attach the emitter and the receiver to a process tool.

20. The metrology tool of claim 14, further comprising a mount configured to position the emitter over a substrate path of a process tool.

21. The metrology tool of claim 14, further comprising a support configured to position the emitter and the receiver over a substrate transport between a first process tool and a second process tool.

22. A metrology method comprising:
emitting multiple wavelength radiation beam onto an area of a production substrate including an anti-reflective layer;
detecting intensities and wavelengths of a reflected radiation beam;
analyzing the intensities and wavelengths to determine a spectrum of the intensities at respective wavelengths;
transforming the spectrum of the intensities into a frequency spectrum;
selecting a suppression band based on an expected wavelength representative of a portion of the anti-reflective layer; and
determining a property of the anti-reflective layer based on a portion of the spectrum in the selected suppression band.

23. The method of claim 22, wherein the area comprises at least a portion of two or more die.

24. The method of claim 22, wherein the anti-reflective layer is over a die comprising one or more features within one or more lower layers.

* * * * *